(12) United States Patent
Sweredoski et al.

(10) Patent No.: US 10,266,866 B2
(45) Date of Patent: Apr. 23, 2019

(54) REDUCTION OF OXIDATED METHIONINE PEPTIDES FOR MASS SPECTROMETRY

(71) Applicant: CALIFORNIA INSTITUTE OF TECHNOLOGY, Pasadena, CA (US)

(72) Inventors: Michael Sweredoski, Altadena, CA (US); Annie Moradian, La Canada, CA (US); Tanya R. Yakushi, Monterey Park, CA (US); Sonja Hess, Arcadia, CA (US); Roxana Eggleston-Rangel, Los Angeles, CA (US)

(73) Assignee: California Institute of Technology, Pasadena, CA (US)

( * ) Notice: Subject to any disclaimer, the term of this patent is extended or adjusted under 35 U.S.C. 154(b) by 0 days.

(21) Appl. No.: 15/360,662

(22) Filed: Nov. 23, 2016

(65) Prior Publication Data

US 2017/0152541 A1    Jun. 1, 2017

Related U.S. Application Data

(60) Provisional application No. 62/258,677, filed on Nov. 23, 2015.

(51) Int. Cl.
| | |
|---|---|
| *C12P 7/00* | (2006.01) |
| *C12P 21/02* | (2006.01) |
| *C12N 9/02* | (2006.01) |
| *C12N 11/08* | (2006.01) |

(52) U.S. Cl.
CPC ............ *C12P 21/02* (2013.01); *C12N 9/0051* (2013.01); *C12N 11/08* (2013.01); *C12Y 108/04011* (2013.01); *C12Y 108/04012* (2013.01)

(58) Field of Classification Search
None
See application file for complete search history.

(56) References Cited

U.S. PATENT DOCUMENTS

| | | |
|---|---|---|
| 5,952,186 A | 9/1999 | Shultz et al. |
| 2002/0106658 A1 | 8/2002 | Wells et al. |
| 2006/0216751 A1 | 9/2006 | Boschetti et al. |

OTHER PUBLICATIONS

Kim et al. (Biochem., vol. 45, 2006, pp. 13697-13704).*
Weiner et al. (JBC, vol. 170, No. 4,1988, pp. 1505-1510).*
International Search Report and Written Opinion for corresponding International Patent Application No. PCT/US2016/063621, dated Apr. 21, 2017, 11 pp.
Goldenberg, Martin I. et al.; "Stability of Specific Bacteriophage Stored on Filter-Paper Strips for the Rapid Identification of *Pasteurella pestis*"; Journal of Bacteriology; Feb. 1965; vol. 89; No. 2; p. 542.
Le, Dung Tien et al.; "Analysis of Methionine/Selenomethionine Oxidation and Methionine Sulfoxide Reductase Function Using Methionine-Rich Proteins and Antibodies against Their Oxidized Forms"; Biochemistry; Jun. 24, 2008; 47(25); pp. 6685-6694.
Tsvetkov, Philipp O. et al.; "Calorimetry and mass spectrometry study of oxidized calmodulin interaction with target and differential repair by methionine sulfoxide reductases"; Biochimie 87; 2005; pp. 473-480.
Douglas, T. et al.; "Methionine sulfoxide reductase a (MsrA) deficiency affects the survival of *Mycobacterium smegmatis* within macrophages"; J Bacteriol.; 2004; vol. 186; No. 11; pp. 3590-3598.
Kalli, Anastasia et al.; "Effect of mass spectrometric parameters on peptide and protein identification rates for shotgun proteomic experiments on an LTQ-orbitrap mass analyzer"; Proteomics; 2012; vol. 12; Issue 1; pp. 21-31.
Kalli, Anastasia et al.; "Evaluation and Optimization of Mass Spectrometric Settings during Data-Dependent Acquisition Mode: Focus on LTQ-Orbitrap Mass Analyzers"; J. Proteome Res.; Jul. 5, 2013; 12(7); pp. 3071-3086.
Moskovitz, Jackob et al.; "Methionine sulfoxide reductase (MsrA) is a regulator of antioxidant defense and lifespan in mammals"; PNAS; Nov. 6, 2001; vol. 98; No. 23; pp. 12920-12925.
Moskovitz, Jackob et al.; "*Escherichia coli* Peptide Methionine Sulfoxide Reductase Gene: Regulation of Expression and Role in Protecting Against Oxidative Damage"; J Bacteriol.; Feb. 1995; vol. 177; No. 3; pp. 502-507.
Moskovitz, Jackob et al.; "Overexpression of peptide-methionine sulfoxide reductase in *Saccharomyces cerevisiae* and human T cells provides them with high resistance to oxidative stress"; PNAS; Nov. 1998; vol. 95; pp. 14071-14075.
Moskovitz, Jackob et al.; "The yeast peptide-methionine sulfoxide reductase functions as an antioxidant in vivo"; PNAS; Sep. 1997; vol. 94; pp. 9585-9589.
Romero, Hernan et al.; "Investigations into the role of the plastidial peptide methionine sulfoxide reductase in response to oxidative stress in Arabidopsis"; Plant Physiol.; Nov. 2004; vol. 136; pp. 3784-3794.
Ruan, Hongyu et al.; "High-quality life extension by the enzyme peptide methionine sulfoxide reductase"; PNAS; Mar. 5, 2002; vol. 99; No. 5; pp. 2748-2753.
St. John, Gregory et al.; "Peptide methionine sulfoxide reductase from *Escherichia coli* and *Mycobacterium tuberculosis* protects bacteria against oxidative damage from reactive nitrogen intermediates"; PNAS; Aug. 2001; vol. 98; No. 17; pp. 9901-9906.
Tarrago, Lionel et al.; "Methionine sulfoxide reductases preferentially reduce unfolded oxidized proteins and protect cells from oxidative protein unfolding"; Journal of Biological Chemistry; Jul. 2012; vol. 287; No. 29; pp. 24448-24459.
Yermolaieva, Olena et al.; "Methionine sulfoxide reductase A protects neuronal cells against brief hypoxia/reoxygenation"; PNAS; Feb. 2004; vol. 101; No. 5; pp. 1159-1164.

* cited by examiner

*Primary Examiner* — Hope Robinson
(74) *Attorney, Agent, or Firm* — Lewis Roca Rothgerber Christie LLP

(57) ABSTRACT

A method for preparing a methionine containing peptide or protein for analysis by mass spectrometry by incubating the methionine containing peptide or protein with a heterologous methionine sulfoxide reductase A (MsrA), a heterologous methionine sulfoxide reductase B (MsrB), or a heterologous methionine sulfoxide reductase AB (MsrAB) enzyme results in the reduction of an oxidized methionine containing peptide or protein.

20 Claims, 13 Drawing Sheets
(12 of 13 Drawing Sheet(s) Filed in Color)

Specification includes a Sequence Listing.

methionine-*S*-sulfoxide methionine-*R*-sulfoxide

GAILTTM(ox)LATR (SEQ ID NO:2) – 582.3263++

GAILTTMLATR (SEQ ID NO:2) – 574.3288++

SEQUENCE LISTING

```
<160> NUMBER OF SEQ ID NOS: 5

<210> SEQ ID NO 1
<211> LENGTH: 15
<212> TYPE: PRT
<213> ORGANISM: Artificial Sequence
<220> FEATURE:
<223> OTHER INFORMATION: Standard peptide 1

<400> SEQUENCE: 1

Thr Ala Gly Thr Ser Phe Met Met Thr Pro Tyr Val Val Thr Arg
1               5                   10                  15

<210> SEQ ID NO 2
<211> LENGTH: 11
```

```
<212> TYPE: PRT
<213> ORGANISM: artificial sequence
<220> FEATURE:
<223> OTHER INFORMATION: Standard peptide 2

<400> SEQUENCE: 2

Gly Ala Ile Leu Thr Thr Met Leu Ala Thr Arg
1               5                   10

<210> SEQ ID NO 3
<211> LENGTH: 1599
<212> TYPE: DNA
<213> ORGANISM: Neisseria meningitidis

<400> SEQUENCE: 3
catatgaaac atcgtacctt cttctccctg tgtgctaaat ttggctgcct gctggccctg      60
ggtgcctgta gtccgaaaat cgttgacgct ggtgccgcaa ccgtcccgca taccctgtcc     120
accctgaaaa ccgcagataa ccgtccggct tcagtttatc tgaagaaaga taaaccgacc     180
ctgattaaat tctgggcctc ctggtgcccg ctgtgtctgt cagaactggg ccagacggaa     240
aaatgggcgc aagatgccaa atttagctct gcaaacctga tcaccgtggc ttcaccgggc     300
tttctgcacg aaaagaaaga tggtgacttc agaaatggt atgcaggcct gaattacccg     360
aaactgccgg tggttacgga taacggcggt accattgcac aatcactgaa tatctcggtt     420
tatccgagct gggctctgat tggcaaagat ggtgacgtgc agcgtattgt taaaggtagt     480
atcaacgaag cccaagcact ggctctgatc cgcgatccga atgcggacct gggctctctg     540
aaacatagtt tctacaaacc ggatacccag aagaaagatt ctaaaatcat gaacacccgt     600
acgatctatc tggcgggcgg ttgcttttgg ggtctggaag cctacttcca gcgcattgat     660
ggcgtcgtgg acgccgtgag tggctatgcc aacggtaata cgaaaaatcc gtcctatgaa     720
gatgtttcat accgtcatac cggtcacgca gaaacggtta agtcaccta tgatgctgac      780
aaactgtctc tggatgacat cctgcagtac tttttccgtg ttgtcgatcc gacgtcgctg     840
aacaaacagg gcaatgacac cggtacgcaa atcgcagcg gcgtctatta caccgatccg      900
gcagaaaaag ctgtgattgc agctgcgctg aaacgcgaac agcaaaaata tcagctgccg     960
ctggttgtgg aaaacgaacc gctgaaaaat ttctacgatg cggaagaata tcatcaagac    1020
tacctgatca aaaacccgaa tggttattgt cacattgata tccgtaaagc ggacgaaccg    1080
ctgccgggca aaaccaaaac ggccccgcag gcaaaggtt ttgatgccgc aacctataaa     1140
aaaccgtccg acgccgaact gaaacgcacc ctgacggaag aacagtacca agtgacgcag    1200
aattcggcga ccgaatatgc ctttagccat gaatacgatc acctgttcaa accgggtatt    1260
tatgttgacg tcgtgagcgg cgaaccgctg tttagttccg cagataaata cgactctggc    1320
tgcggttggc cgagtttcac gcgtccgatc gatgcgaaat ctgtgaccga acatgatgac    1380
tttagttata acatgcgtcg caccgaagtt cgctcgcacg ctgcggatag ccatctgggc    1440
cacgtctttc cggatggtcc gcgtgacaaa ggcggtctgc gctactgtat taatggtgcc    1500
agcctgaaat ttatcccgct ggaacaaatg gacgctgccg gttatggcgc tctgaaatca    1560
aaagtcaaac atcatcacca tcaccactag taaggatcc                           1599

<210> SEQ ID NO 4
<211> LENGTH: 522
<212> TYPE: PRT
<213> ORGANISM: Neisseria meningitidis

<400> SEQUENCE: 4
```

Met Lys His Arg Thr Phe Phe Ser Leu Cys Ala Lys Phe Gly Cys Leu
1               5                   10                  15

Leu Ala Leu Gly Ala Cys Ser Pro Lys Ile Val Asp Ala Gly Ala Ala
            20                  25                  30

Thr Val Pro His Thr Leu Ser Thr Leu Lys Thr Ala Asp Asn Arg Pro
                35                  40                  45

Ala Ser Val Tyr Leu Lys Lys Asp Lys Pro Thr Leu Ile Lys Phe Trp
    50                  55                  60

Ala Ser Trp Cys Pro Leu Cys Leu Ser Glu Leu Gly Gln Thr Glu Lys
65                  70                  75                  80

Trp Ala Gln Asp Ala Lys Phe Ser Ser Ala Asn Leu Ile Thr Val Ala
                85                  90                  95

Ser Pro Gly Phe Leu His Glu Lys Lys Asp Gly Asp Phe Gln Lys Trp
                100                 105                 110

Tyr Ala Gly Leu Asn Tyr Pro Lys Leu Pro Val Val Thr Asp Asn Gly
            115                 120                 125

Gly Thr Ile Ala Gln Ser Leu Asn Ile Ser Val Tyr Pro Ser Trp Ala
    130                 135                 140

Leu Ile Gly Lys Asp Gly Asp Val Gln Arg Ile Val Lys Gly Ser Ile
145                 150                 155                 160

Asn Glu Ala Gln Ala Leu Ala Leu Ile Arg Asp Pro Asn Ala Asp Leu
                165                 170                 175

Gly Ser Leu Lys His Ser Phe Tyr Lys Pro Asp Thr Gln Lys Lys Asp
                180                 185                 190

Ser Lys Ile Met Asn Thr Arg Thr Ile Tyr Leu Ala Gly Gly Cys Phe
        195                 200                 205

Trp Gly Leu Glu Ala Tyr Phe Gln Arg Ile Asp Gly Val Val Asp Ala
    210                 215                 220

Val Ser Gly Tyr Ala Asn Gly Asn Thr Lys Asn Pro Ser Tyr Glu Asp
225                 230                 235                 240

Val Ser Tyr Arg His Thr Gly His Ala Glu Thr Val Lys Val Thr Tyr
                245                 250                 255

Asp Ala Asp Lys Leu Ser Leu Asp Ile Leu Gln Tyr Phe Phe Arg
                260                 265                 270

Val Val Asp Pro Thr Ser Leu Asn Lys Gln Gly Asn Asp Thr Gly Thr
        275                 280                 285

Gln Tyr Arg Ser Gly Val Tyr Tyr Thr Asp Pro Ala Glu Lys Ala Val
    290                 295                 300

Ile Ala Ala Ala Leu Lys Arg Glu Gln Gln Lys Tyr Gln Leu Pro Leu
305                 310                 315                 320

Val Val Glu Asn Glu Pro Leu Lys Asn Phe Tyr Asp Ala Glu Glu Tyr
                325                 330                 335

His Gln Asp Tyr Leu Ile Lys Asn Pro Asn Gly Tyr Cys His Ile Asp
                340                 345                 350

Ile Arg Lys Ala Asp Glu Pro Leu Pro Gly Lys Thr Lys Thr Ala Pro
                355                 360                 365

Gln Gly Lys Gly Phe Asp Ala Ala Thr Tyr Lys Lys Pro Ser Asp Ala
    370                 375                 380

Glu Leu Lys Arg Thr Leu Thr Glu Glu Gln Tyr Gln Val Thr Gln Asn
385                 390                 395                 400

Ser Ala Thr Glu Tyr Ala Phe Ser His Glu Tyr Asp His Leu Phe Lys
                405                 410                 415

```
Pro Gly Ile Tyr Val Asp Val Val Ser Gly Glu Pro Leu Phe Ser Ser
            420             425             430

Ala Asp Lys Tyr Asp Ser Gly Cys Gly Trp Pro Ser Phe Thr Arg Pro
        435             440             445

Ile Asp Ala Lys Ser Val Thr Glu His Asp Asp Phe Ser Tyr Asn Met
        450             455             460

Arg Arg Thr Glu Val Arg Ser His Ala Ala Asp Ser His Leu Gly His
465             470             475             480

Val Phe Pro Asp Gly Pro Arg Asp Lys Gly Gly Leu Arg Tyr Cys Ile
                485             490             495

Asn Gly Ala Ser Leu Lys Phe Ile Pro Leu Glu Gln Met Asp Ala Ala
            500             505             510

Gly Tyr Gly Ala Leu Lys Ser Lys Val Lys
            515             520

<210> SEQ ID NO 5
<211> LENGTH: 528
<212> TYPE: PRT
<213> ORGANISM: Neisseria meningitidis

<400> SEQUENCE: 5

Met Lys His Arg Thr Phe Phe Ser Leu Cys Ala Lys Phe Gly Cys Leu
1               5                   10                  15

Leu Ala Leu Gly Ala Cys Ser Pro Lys Ile Val Asp Ala Gly Ala Ala
            20                  25                  30

Thr Val Pro His Thr Leu Ser Thr Leu Lys Thr Ala Asp Asn Arg Pro
        35                  40                  45

Ala Ser Val Tyr Leu Lys Lys Asp Lys Pro Thr Leu Ile Lys Phe Trp
    50                  55                  60

Ala Ser Trp Cys Pro Leu Cys Leu Ser Glu Leu Gly Gln Thr Glu Lys
65                  70                  75                  80

Trp Ala Gln Asp Ala Lys Phe Ser Ser Ala Asn Leu Ile Thr Val Ala
                85                  90                  95

Ser Pro Gly Phe Leu His Glu Lys Lys Asp Gly Asp Phe Gln Lys Trp
            100                 105                 110

Tyr Ala Gly Leu Asn Tyr Pro Lys Leu Pro Val Val Thr Asp Asn Gly
        115                 120                 125

Gly Thr Ile Ala Gln Ser Leu Asn Ile Ser Val Tyr Pro Ser Trp Ala
    130                 135                 140

Leu Ile Gly Lys Asp Gly Asp Val Gln Arg Ile Val Lys Gly Ser Ile
145                 150                 155                 160

Asn Glu Ala Gln Ala Leu Ala Leu Ile Arg Asp Pro Asn Ala Asp Leu
                165                 170                 175

Gly Ser Leu Lys His Ser Phe Tyr Lys Pro Asp Thr Gln Lys Lys Asp
            180                 185                 190

Ser Lys Ile Met Asn Thr Arg Thr Ile Tyr Leu Ala Gly Gly Cys Phe
        195                 200                 205

Trp Gly Leu Glu Ala Tyr Phe Gln Arg Ile Asp Gly Val Val Asp Ala
    210                 215                 220

Val Ser Gly Tyr Ala Asn Gly Asn Thr Lys Asn Pro Ser Tyr Glu Asp
225                 230                 235                 240

Val Ser Tyr Arg His Thr Gly His Ala Glu Thr Val Lys Val Thr Tyr
                245                 250                 255

Asp Ala Asp Lys Leu Ser Leu Asp Asp Ile Leu Gln Tyr Phe Phe Arg
            260                 265                 270
```

```
Val Val Asp Pro Thr Ser Leu Asn Lys Gln Gly Asn Asp Thr Gly Thr
        275                 280                 285

Gln Tyr Arg Ser Gly Val Tyr Tyr Thr Asp Pro Ala Glu Lys Ala Val
    290                 295                 300

Ile Ala Ala Ala Leu Lys Arg Glu Gln Gln Lys Tyr Gln Leu Pro Leu
305                 310                 315                 320

Val Val Glu Asn Glu Pro Leu Lys Asn Phe Tyr Asp Ala Glu Glu Tyr
                325                 330                 335

His Gln Asp Tyr Leu Ile Lys Asn Pro Asn Gly Tyr Cys His Ile Asp
            340                 345                 350

Ile Arg Lys Ala Asp Glu Pro Leu Pro Gly Lys Thr Lys Thr Ala Pro
        355                 360                 365

Gln Gly Lys Gly Phe Asp Ala Ala Thr Tyr Lys Lys Pro Ser Asp Ala
    370                 375                 380

Glu Leu Lys Arg Thr Leu Thr Glu Glu Gln Tyr Gln Val Thr Gln Asn
385                 390                 395                 400

Ser Ala Thr Glu Tyr Ala Phe Ser His Glu Tyr Asp His Leu Phe Lys
                405                 410                 415

Pro Gly Ile Tyr Val Asp Val Val Ser Gly Glu Pro Leu Phe Ser Ser
            420                 425                 430

Ala Asp Lys Tyr Asp Ser Gly Cys Gly Trp Pro Ser Phe Thr Arg Pro
        435                 440                 445

Ile Asp Ala Lys Ser Val Thr Glu His Asp Asp Phe Ser Tyr Asn Met
    450                 455                 460

Arg Arg Thr Glu Val Arg Ser His Ala Ala Asp Ser His Leu Gly His
465                 470                 475                 480

Val Phe Pro Asp Gly Pro Arg Asp Lys Gly Gly Leu Arg Tyr Cys Ile
                485                 490                 495

Asn Gly Ala Ser Leu Lys Phe Ile Pro Leu Glu Gln Met Asp Ala Ala
            500                 505                 510

Gly Tyr Gly Ala Leu Lys Ser Lys Val Lys His His His His His His
            515                 520                 525
```

REDUCTION OF OXIDATED METHIONINE PEPTIDES FOR MASS SPECTROMETRY

CROSS-REFERENCE TO RELATED APPLICATION(S)

The present application claims priority to and the benefit of U.S. Provisional Application Ser. No. 62/258,677 filed on Nov. 23, 2015, entitled "Device to Reduce Oxidized Amino Acid Residues," the entire content of which is incorporated herein by reference.

INCORPORATION BY REFERENCE

The instant application contains a Sequence Listing which has been submitted electronically in ASCII format and is hereby incorporated by reference in its entirety. Said ASCII copy, created on Feb. 8, 2017, is named 130466SEQLISTING.txt and is 11,995 bytes in size.

BACKGROUND

Proteomics has moved beyond the cataloguing of proteins towards the quantification of proteomic changes between two or more conditions. These proteomic changes may be quantified using a traditional shotgun analysis or using a more targeted mass spectrometry (MS) analysis such as single reaction monitoring (SRM), multiple reaction monitoring (MRM) or parallel reaction monitoring (PRM). Targeted MS analyses require proteotypic peptides that are reproducibly selected in each analysis. For a peptide to be considered proteotypic, it needs to be observable by mass spectrometry. In addition, it needs to be unique for the protein it is representing, and ideally without post-translational or chemically induced modifications. The general recommendation is also to avoid peptides that contain methionines since methionines are prone to oxidation.

However, these conditions imposed on proteotypic peptides limit the applicability of targeted analyses when a biological study requires the analysis of a peptide that contains a methionine or may be post-translationally modified. There are a substantial number of methionine-containing peptides that are important in biological studies. An example of a methionine-containing peptide includes TAGTSFMMTPYVVTR (SEQ ID NO: 1) from c-jun N-terminal kinase-1 or GAILTTMLATR (SEQ ID NO: 2) from Ca2+/calmodulin-dependent protein kinase II (CaMKII), which is known to be modulated during memory and learning, and thus, it is more effective and efficient if they can be quantified when studied in this context. To study methionine-containing peptides, they would have to be monitored in their oxidized and reduced forms. If additional post-translational modifications are to be studied, the number of necessary transitions quickly increases.

SUMMARY

In some embodiments of the present invention, a method for preparing a methionine-containing peptide or protein for analysis by mass spectrometry includes incubating the methionine-containing peptide or protein with a heterologous methionine sulfoxide reductase (Msr) enzyme. In some embodiments, the heterologous Msr enzyme is a heterologous MsrA protein, a heterologous MsrB protein, and/or a heterologous MsrAB protein.

In some embodiments of the present invention, a method for preparing a methionine-containing peptide or protein for analysis by mass spectrometry includes immobilizing the heterologous Msr enzyme, adding the methionine-containing peptide or protein to the immobilized heterologous Msr enzyme, and separating the methionine-containing peptide or protein from the immobilized heterologous Msr enzyme after incubation. In some embodiments of the present invention, the method also includes activating the heterologous Msr enzyme prior to adding the methionine-containing peptide or protein.

In some embodiments of the present invention, a method for preparing a methionine-containing peptide or protein for analysis by mass spectrometry includes immobilizing a heterologous Msr enzyme on a resin bead or a membrane filter, activating the immobilized heterologous Msr enzyme, adding the methionine-containing peptide or protein to the heterologous Msr enzyme, and separating the methionine-containing peptide or protein from the immobilized heterologous Msr enzyme after incubation.

In some embodiments of the present invention, a kit for reducing a methionine-containing peptide or protein includes a heterologous methionine sulfoxide reductase (Msr) enzyme. In some embodiments, the heterologous Msr enzyme in the kit is a heterologous MsrA protein, a heterologous MsrB protein, and/or a heterologous MsrAB protein. In some embodiments, the Msr enzyme is lyophilized on a membrane filter.

BRIEF DESCRIPTION OF THE DRAWINGS

The patent or application file contains at least one drawing executed in color. Copies of this patent or patent application publication with color drawings will be provided by the Office upon request and payment of the necessary fee.

DETAILED DESCRIPTION

Figure 1A:
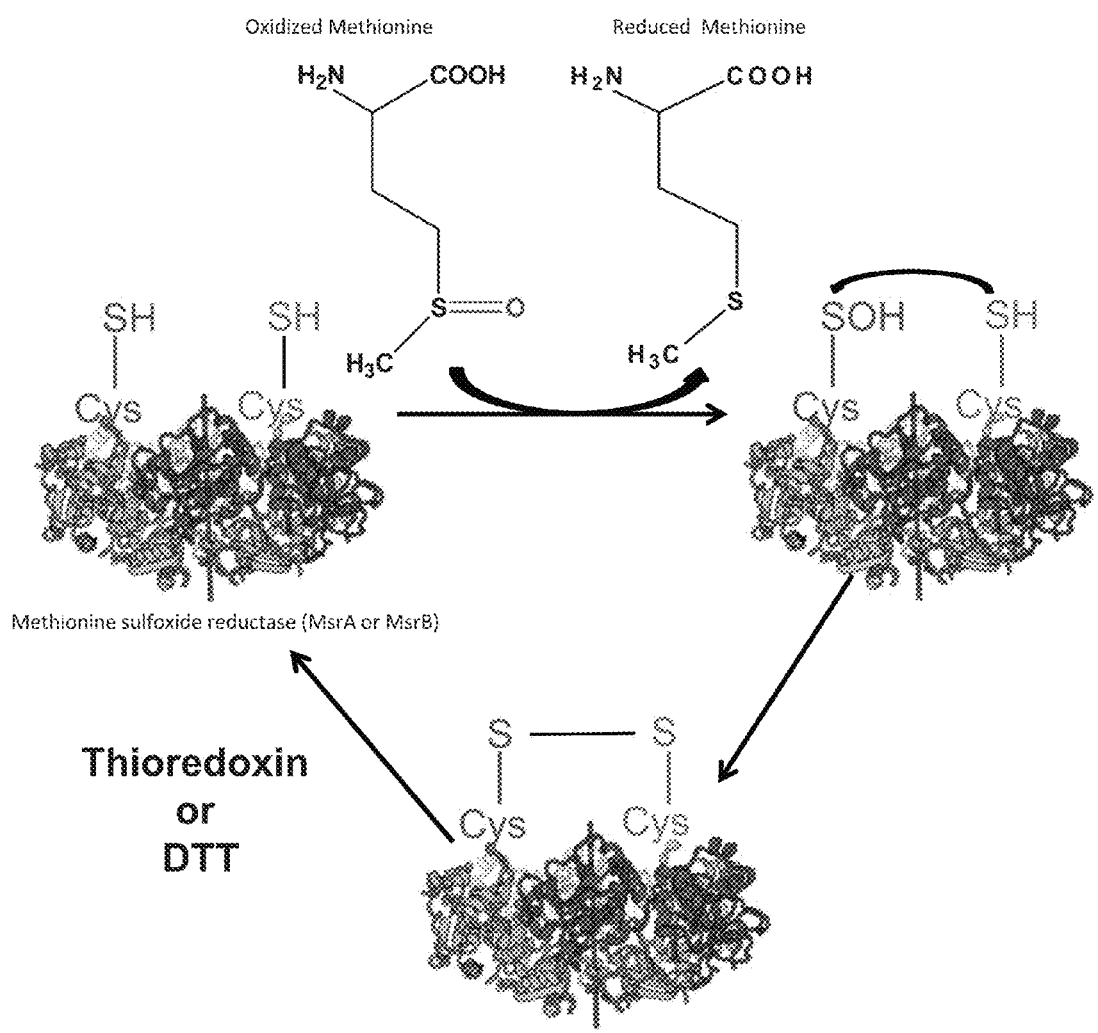
FIG. 1A is a schematic depiction of the catalytic mechanism of the methionine sulfoxide reductases MsrA and MsrB according to embodiments of the present invention, in which the nucleophilic, catalytic cysteine of the Msr protein (Cys, shown in red) attacks the sulfoxide of the methionine, which leads to a sulfenic acid formation of the cysteine and the release of the reduced methionine. The second cysteine (Cys, shown in blue) attacks the sulfenic acid, thereby forming a disulfide bond. The Msr enzyme is regenerated by reduction of the disulfide bond (e.g., by DTT).
Figure 1B:
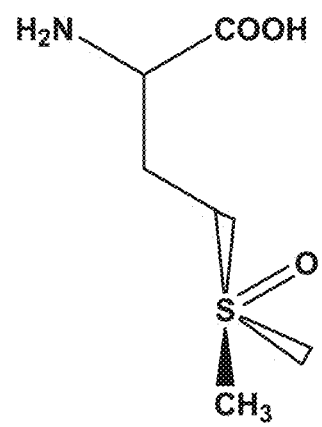
FIG. 1B shows the structures of the pro-chiral forms of methionine-S-sulfoxide and methionine-R-sulfoxide.
Figure 1B:
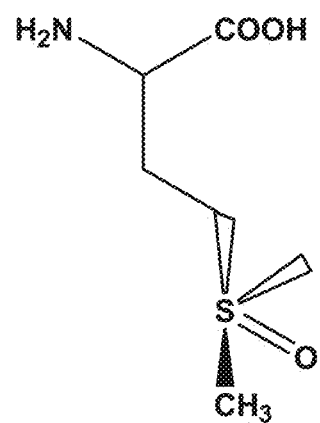

Methionine sulfoxide reductase A (MsrA) and methionine sulfoxide reductase B (MsrB) are two enzymes that stereospecifically reduce peptide-methionine (S)-sulfoxides and (R)-sulfoxides, respectively, to methionine, as shown schematically in FIGS. 1A and 1B. In most organisms, the two enzymes are encoded by two separate genes, however, some microorganisms such as Neisseria sp. express one enzyme (MsrAB) that includes both MsrA and MsrB domains.

Embodiments of the present invention include methods for preparing a methionine-containing peptide or protein for routine mass spectrometry analysis by reducing the oxidized methionine residues in a peptide or protein. Methods for reducing oxidized methionine residues in a peptide or protein include incubating the peptide or protein with a methionine sulfoxide reductase A (MsrA) enzyme, a methionine sulfoxide reductase B (MsrB) enzyme, or a methionine sulfoxide reductase AB (MsrAB) enzyme. As used herein, "incubating" and like terms refer to the mixing of the Msr enzyme and a methionine-containing peptide or protein to allow for molecular interaction of the Msr enzyme and the methionine-containing peptide or protein. In some embodiments, a method for reducing oxidized methionine in a peptide or protein includes incubating the peptide or protein with at least one of MsrA, MsrB, or MsrAB enzyme. In other embodiments, a method for reducing oxidized methionine in a peptide or protein includes incubating the peptide or protein with both MsrA and MsrB enzymes or an MsrAB enzyme.

Methionine sulfoxide reductase (Msr) enzymes are found in biological organisms from bacteria to man, including plants, as described, for example, in Moskovitz et al, "Methionine sulfoxide reductase (MsrA) is a regulator of antioxidant defense and lifespan in mammals," *PNAS*, 2001; 98:12920-12925; Moskovitz et al., "The yeast peptide-methionine sulfoxide reductase functions as an antioxidant in vivo," *PNAS*, 1997; 94:9585-9589; Moskovitz et al., "*Escherichia coli* peptide methionine sulfoxide reductase gene: regulation of expression and role in protecting against oxidative damage," *J Bacteriol.* 1995; 177:502-507; Douglas et al., "Methionine sulfoxide reductase A (MsrA) deficiency affects the survival of *Mycobacterium smegmatis* within macrophages," *J Bacteriol.* 2004; 186:3590-3598; St John et al., "Peptide methionine sulfoxide reductase from *Escherichia coli* and *Mycobacterium tuberculosis* protects bacteria against oxidative damage from reactive nitrogen intermediates," *PNAS*, 2001; 98:9901-9906; Ruan et al., "High-quality life extension by the enzyme peptide methionine sulfoxide reductase," *PNAS*, 2002; 99:2748-2753; Moskovitz et al., "Overexpression of peptide-methionine sulfoxide reductase in *Saccharomyces cerevisiae* and human T cells provides them with high resistance to oxidative stress," *PNAS*, 1998; 95:14071-14075; Romero et al., "Investigations into the role of the plastidial peptide methionine sulfoxide reductase in response to oxidative stress in *Arabidopsis*," *Plant Physiol*, 2004; 136:3784-3794; and Yermolaieva et al., "Methionine sulfoxide reductase A protects neuronal cells against brief hypoxia/reoxygenation," *PNAS*, 2004; 101:1159-1164, the entire contents of all of which are incorporated herein by reference. Accordingly, as methionine is found throughout all living organisms, and the structure of methionine is the same in all organisms, a heterologously expressed Msr enzyme (MsrA, MsrB, or MsrAB) from a suitable organism may be used to catalyze the reduction of oxidized methionine in peptides or proteins.

In some embodiments of the present invention, an Msr enzyme is immobilized on a substrate to facilitate incubation of the enzyme with a peptide, multiple peptides, a cell lysate of peptides, a protein, or multiple proteins. As used herein, "immobilized," "immobilizing," and like terms with respect to the Msr enzyme refers to the addition of the Msr enzyme to a substrate from which it is not released upon washing, incubation, or elution of a methionine-containing peptide or protein. In some embodiments, an Msr enzyme is immobilized on a substrate using any suitable method. For example, an Msr enzyme may be immobilized on a resin bead.

Figure 2:
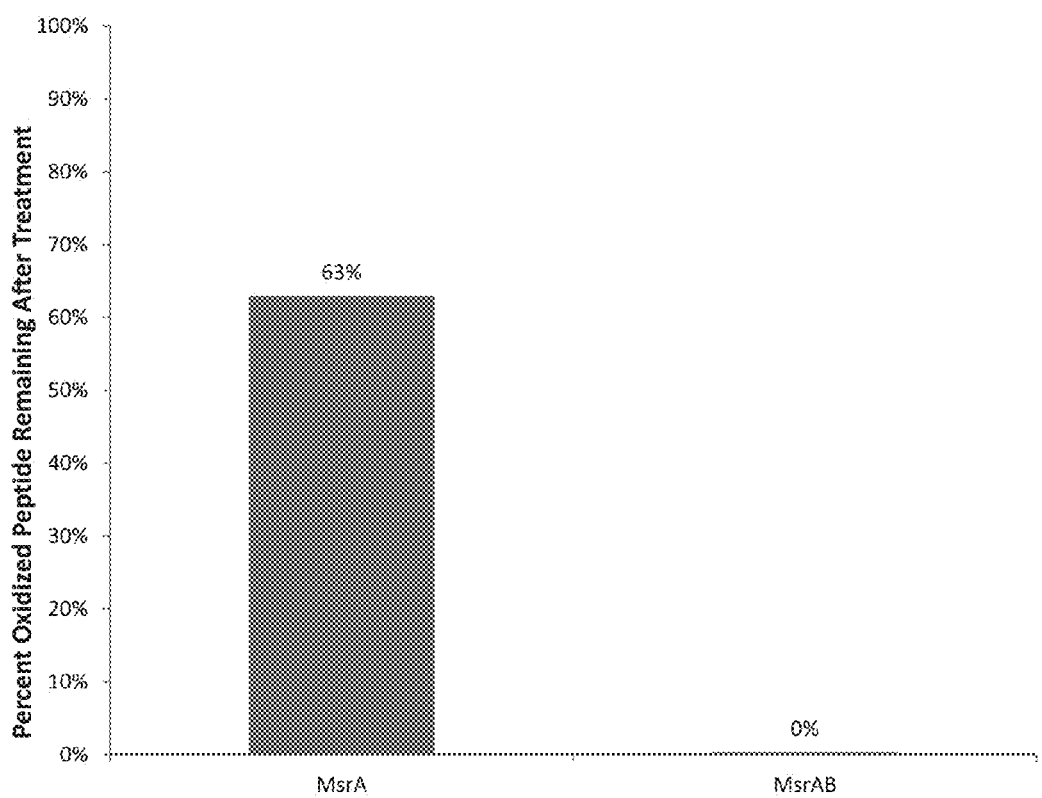
FIG. 2 is a graph showing the relative amount of the oxidized peptide TAGTSFMMTPYWTR (SEQ ID NO; 1) after treatment with MsrA enzyme (left as indicated, shown in blue) or MsrAB (right) as indicated, as measured by MS, according to embodiments of the present invention.

Non-limiting examples of resin beads include agarose resin beads, magnetic resin beds, and tagged resin beads (e.g., streptavidin beads). Suitable resin beads may be of various sizes ranging from 5 um to 500 um. For example, MsrA enzyme may be coupled to agarose beads and incubated with a commercially available peptide (TAGTSFMMTPYVVTR) (SEQ ID NO: 1). After incubation with the MsrA enzyme-coupled beads, the peptide (SEQ ID NO: 1) may be eluted (separated from the MsrA enzyme) with TRIS buffer and analyzed by mass spectrometry (MS). As shown in FIG. 2, MsrA enzyme alone reduced 37% of the TAGTSFMMTPYVVTR (SEQ ID NO: 1) peptide, with 63% oxidized peptide remaining.

In some embodiments of the present invention, an Msr enzyme may be immobilized on a membrane filter by the addition of the Msr enzyme to a membrane filter. Membrane filters may be made of cellulose. In some embodiments, the membrane filters are incorporated into a centrifuge tube. Non-limiting examples of membrane filters include cellulose membrane filters that restrict the size of the peptides or proteins that pass through the pores of the membrane filter, thereby allowing for a separation of the peptide or protein from the Msr enzyme after incubation with the Msr enzyme. For example, membrane filters (e.g., manufactured by Amicon®) having a nominal molecular weight limit (NMWL) or molecular weight cutoff (MWCO) of 3 kilodalton (kDa) or 10 kDa may be used to immobilize an Msr enzyme or enzymes. For example, the MsrAB enzyme is 58 kDa and will not pass through a 3 kDa or 10 kDa filter. As shown in FIG. 2, MsrAB immobilized on a membrane filter was able to reduce all of the methionines in the SEQ ID NO: 1 peptide sample.

In some embodiments of the present invention, a membrane filter for immobilization of an Msr enzyme has a nominal molecular weight limit (NMWL) or molecular weight cutoff (MWCO) that is less than the molecular weight of the MsrA, MsrB, or MsrAB enzyme and greater than the molecular weight of any of the methionine-containing peptides or proteins to be analyzed.

Figure 3A:
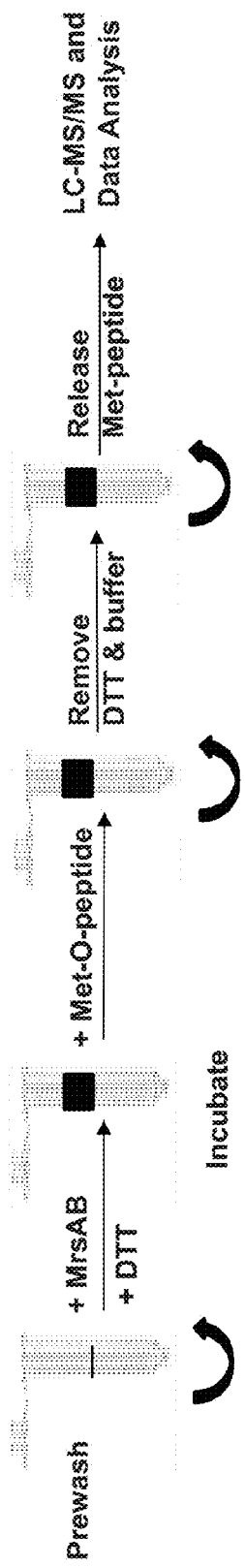
FIG. 3A is a schematic of a workflow for methionine sulfoxide reduction using MsrAB enzyme added to a membrane filter, according to embodiments of the present invention.
Figure 3B:
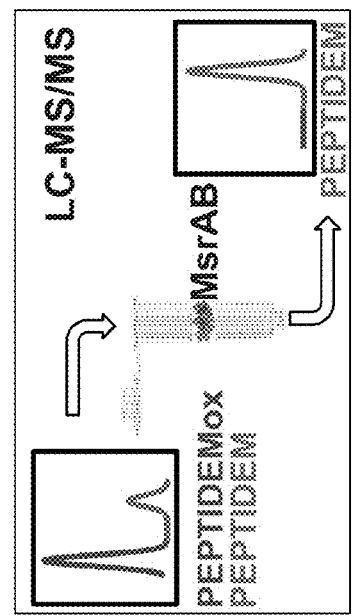
FIG. 3B is a schematic showing a representative mass spectrometry (MS) extracted ion chromatogram (XIC) of an untreated methionine-containing peptide having both oxidized (PEPTIDEMox shown in red) and reduced (PEPTIDEM shown in blue) forms and corresponding MS peaks, and an MS XIC of a treated (with MsrAB enzyme) methionine-containing peptide without oxidized peaks, according to embodiments of the present invention.

In some embodiments of the present invention, a method for immobilizing an Msr enzyme on a membrane filter includes prewashing the membrane filter, loading the Msr enzyme or enzymes (MsrA, MsrB, or MsrAB) onto the filter, activating the Msr enzyme using a reducing agent (e.g., DTT), incubating the activated Msr enzyme with a peptide or protein, washing the enzyme and peptide/protein reaction, and releasing the peptide/protein from the filter. The Msr-treated peptide/protein found in the flow through is then analyzed, for example, by mass spectrometry (MS). A schematic of this Msr-immobilized work flow method is shown in FIG. 3A. A schematic showing representative extracted ion chromatograms (XICs) of oxidized and reduced peptides before and after Msr enzyme treatment is shown in FIG. 3B.

In some embodiments of the present invention, the membrane filter is incubated with a blocking agent prior to incubation with a methionine-containing peptide or protein. Non-limiting examples of a blocking agent include bovine serum albumin (BSA), milk, or casein protein.

In some embodiments of the present invention, the reduction of a methionine-containing peptide or protein using an Msr enzyme is carried out using a buffer compatible with the Msr enzyme, the peptide or proteins, and with the subsequent MS analysis. In some embodiments, the buffer for the Msr-enzyme reduction reaction is a Tris or ammonium bicarbonate buffer. As shown in FIG. 4B, both Tris and ammonium bicarbonate (Ambic) buffers are compatible with the Msr enzymatic reduction reaction.

In some embodiments of the present invention, the Msr enzyme is "activated" prior to incubation with a methionine-containing peptide or protein to ensure reduction of the disulfide bonds in the Msr enzyme as shown in FIG. 1A. As used herein, "activated," "activating," and like terms with respect to the Msr enzyme refer to the treatment of the Msr enzyme with a reducing agent to reduce the disulfide bonds rendering the enzyme enzymatically active for reducing oxidized methionine. The Msr enzyme may be activated using a reducing agent such as dithiothreitol (DTT) or thioredoxin. In some embodiments of the present invention, the Msr enzyme is activated with 10 mM to 50 mM DTT. In some embodiments of the present invention, the Msr enzyme is activated with 15 mM to 40 mM DTT. In some embodiments of the present invention, the Msr enzyme is activated with 15 to 30 mM DTT.

In some embodiments of the present invention, after incubation of the peptide or protein with Msr enzyme, the peptide or protein is released (eluted) or separated from the immobilized Msr enzyme. For example, a peptide or protein after incubation with an Msr enzyme immobilized to agarose beads may be eluted using a Tris buffer. In some embodiments, a peptide or protein after incubation with an Msr enzyme immobilized on a membrane filter may be eluted using an organic solvent. Non-limiting examples of suitable organic solvents for elution include methanol or acetonitrile. Additionally, a mixture of methanol and acetonitrile may be used. In some embodiments, the elution buffer contains 1 part organic solvent (e.g., methanol, acetonitrile, or any mixture thereof) and 1 part water. Some commercially available membrane filters are not compatible with more than 20% acetonitrile.

In some embodiments of the present invention, a kit for reducing methionine-containing peptides or proteins includes an Msr enzyme. The Msr enzyme may be MsrA enzyme, MsrB enzyme, and/or MsrAB enzyme. In some embodiments, the kit includes lyophilized (i.e., freeze dried) Msr enzyme. For example, the kit may include a lyophilized Msr enzyme on a membrane filter or resin bead. In addition to the Msr enzyme, the kit may include Tris or ammonium bicarbonate buffer; 10 mM to 50 mM DTT or thioredoxin for activating the Msr enzyme on the filter; and/or an elution buffer for releasing the Msr-treated peptide or protein from the filter. In some embodiments, the elution buffer is 50% methanol and 50% water or 50% acetonitrile and 50% water. In other embodiments, the elution buffer is 20% acetonitrile, 30% methanol and 50% water.

The following Examples are presented for illustrative purposes only, and do not limit the scope or content of the present application.

EXAMPLES

Example 1. Reduction Experiments Using Commercially Available MsrA

Initial experiments were designed with commercially available MsrA and commercially available standard peptides TAGTSFMMTPYVVTR (SEQ ID NO: 1) and GAILTTMLATR (SEQ ID NO: 2). Peptide synthesis was confirmed by liquid chromatography mass spectrometry (LC-MS). The level of oxidation of the peptides increased over the course of this study (greater than 2 years) during storage in the freezer. Accordingly, the untreated control was always analyzed with the treated (reduced) sample.

To reduce the methionine in these peptides, commercially available MrsA enzyme was coupled to Affi-Gel® 10 beads (Bio-Rad, Hercules, Calif.), and tested for its ability to reduce oxidized methionines in these standard peptides. An aliquot (5 pmol) was added to the activated enzyme on the beads and incubated for 1 hour. The peptides were eluted with TRIS buffer and desalted by Zip Tip® (Sigma-Aldrich) prior to LC-MS analysis. As shown in FIG. 2, MrsA enzyme reduces approximately 37% of all oxidized methionines in standard peptide TAGTSFMMTPYVVTR (SEQ ID NO: 1), indicating efficient reduction of all methionine-S-sulfoxides. Using MrsAB, a complete (approximately 100%) reduction of all methionine-S-sulfoxides and methionine-R-sulfoxides was observed.

Affi-Gel® 10 agarose beads were buffer exchanged from 50 mM Tris, pH 7.6 to 50 mM MOPS, pH7.4. MsrA protein (0.71 nmol=20 μg) was coupled to the 100 μl slurry of Affi-Gel® 10 and free remaining sites were blocked with 100 mM Tris. MsrA protein was reduced with 15 mM DTT in 25 mM TRIS, pH 7.4 for 15 min at 37° C. Standard peptide TAGTSFMMTPYVVTR (SEQ ID NO: 1) (10 pmol) was incubated with the MsrA-slurry for 1 hour at 37° C. Peptides were eluted with 25 mM TRIS, pH 7.4, desalted using ZIP-tips and dried down prior to LC-MS/MS analysis. Samples were analyzed on Orbitrap® Classic (MsrA) and Orbitrap® Elite (MsrAB) (Orbitrap® Classic and Elite were obtained from ThermoFisher Scientific).

Example 2. Preparation of MsrAB and Membrane Filter Reaction Tubes

To efficiently reduce both, methionine-S-sulfoxides and methionine-R-sulfoxides, an enzyme with domains for MsrA and MsrB was needed. Therefore, MsrAB from *Neisseria meningitidis* was expressed in *E. coli* and purified using nickel (Ni) affinity columns. Instead of coupling MsrAB to beads, purified MsrAB was added to a prewashed Amicon® filter (Sigma-Aldrich) with a 3 and 10 kDa cutoff, respectively. Since MsrAB has a molecular weight of greater than 58 kDa, it will be retained on theses filters. The workflow that was developed in the course of this study is shown in FIG. 3A and FIG. 3B. Prewashing Amicon® filters with 20% acetonitrile or 50% methanol reduced the singly charged components (likely plasticizer added during the manufacturing process) that would otherwise contaminate the mass spectrometers during analysis. Note that higher concentrations of acetonitrile are not compatible with the filters. Prior to loading the MsrAB enzyme, the Amicon® filter was conditioned using a Tris or ammonium bicarbonate buffer. To activate the enzyme, DTT was added. Then the oxidized methionine-containing peptide was added and incubated. Excess DTT and the buffer were spun down, and the filter was washed with water. Finally, the reduced peptide was released with 50% MeOH/50% water by centrifugation (FIG. 3A). Excess solvent was evaporated. The dry peptides were redissolved in water and analyzed by mass spectrometry.

Example 3. Optimization Studies

Previously reported $k_{cat}$ values for MsrA and MsrB range between 1 s-1 and 13 s-1 suggesting that a short incubation time (60 min) should be sufficient for enzymatic turnover, as described in Tarrago et al., 2012, *JBC*, 287:24448-24459, the entire content of which is incorporated herein. Longer incubation times did not improve the reductive efficiency of the enzyme. To determine how the methionine-reduced peptides could be best released from the enzyme, different acetonitrile and methanol concentrations were tested. Since Amicon® filters are not compatible with more than 20% acetonitrile, and in fact leach contaminants in the sample, the addition of methanol/water (50:50) was found to be the best releasing buffer for reacted peptides.

Figure 4A:
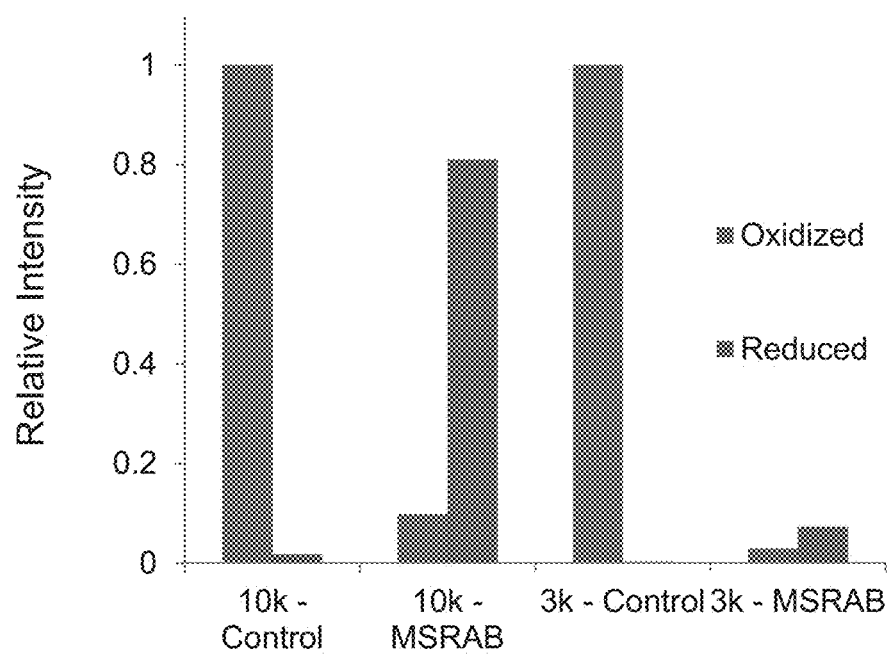
FIG. 4A shows relative amounts (relative intensity) of oxidized (blue) or reduced (red) peptides after incubation with MsrAB or Control using a 10 kilodalton or 3 kilodalton cut-off filter as measured by MS, according to embodiments of the present invention.
Figure 4B:
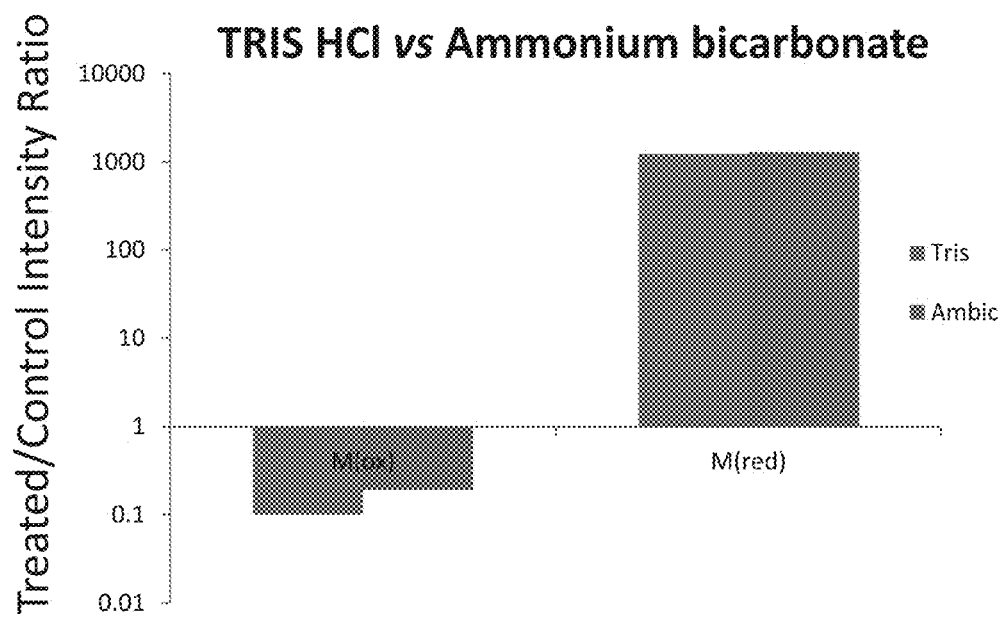
FIG. 4B shows the treated/control intensity ratio of oxidized methionine-containing peptides (M(ox)) and reduced methionine-containing peptides (M(red)) in Tris buffer (Tris)(blue) or Ammonium Bicarbonate (Ambic)(red) as measured by MS, according to embodiments of the present invention.
Figure 4C:
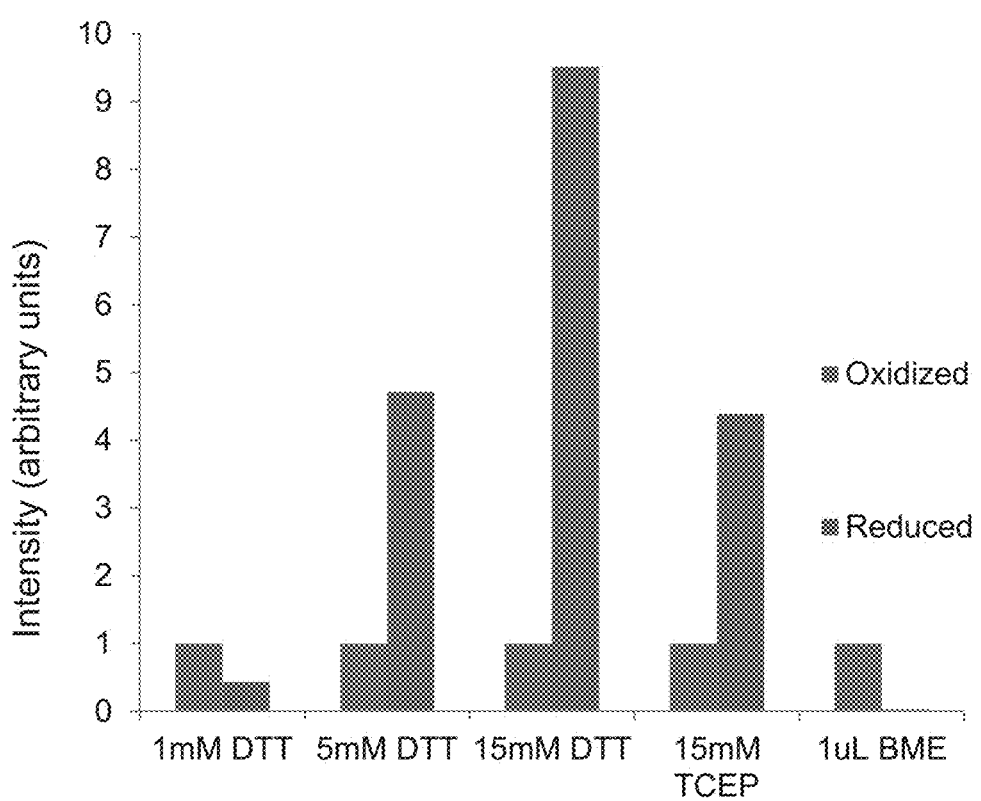
FIG. 4C shows relative amounts (relative intensity) of oxidized (blue) and reduced (red) peptides in the presence of MsrAB or Control that is activated and regenerated in the presence of the reducing agent dithiothreitol (DTT), tris(2-carboxyethyl)phosphine (TCEP), or β-mercaptoethanol (BME) as measured by MS, according to embodiments of the present invention.
Figure 4D:
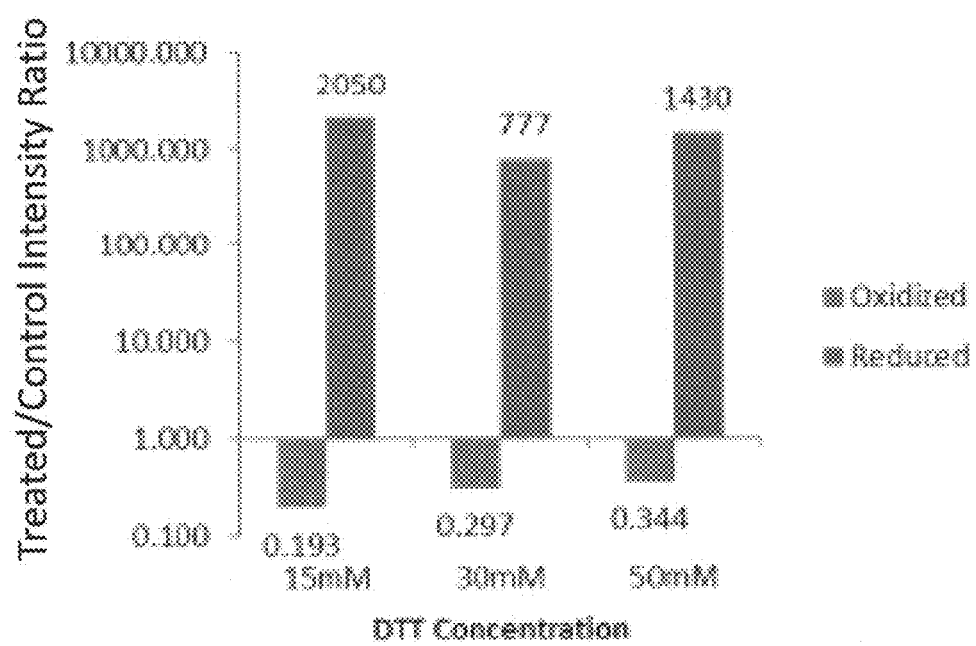
FIG. 4D shows relative amounts of MsrAB treated peptide to control (untreated) peptide with activation of the MsrAB enzyme in the presence of 15 mM, 30 mM, or 50 mM DTT, as indicated, with oxidized peptides shown in blue and reduced peptides shown in red, according to embodiments of the present invention.

As shown in FIG. 4A, recovery of reduced methionine containing peptides indicating almost complete elimination of the oxidized methionines was better in 10 kDa cutoff filters than in 3 kDa cutoff filters. Therefore, for subsequent peptide analyses 10 kDa cutoff filters were used. To improve mass spectrometry compatibility, it was tested whether a volatile ammonium bicarbonate buffer instead of the standard TRIS buffer would yield better results. This step would eliminate the need to desalt the peptides prior to mass spectrometry. FIG. 4B shows that the ammonium bicarbonate (Ambic) is compatible with the enzymatic reduction and that the elimination of an additional desalting step led to similar recovery when ammonium bicarbonate was used vs. TRIS. Subsequent analyses were done using either TRIS or ammonium bicarbonate. As shown in FIG. 1A, the effective reduction of the disulfide bond regenerates and activates the Msr enzyme. Accordingly, various amounts of DTT (1 mM, 5 mM, 15 mM, 30 mM and 50 mM) were tested, and 15 mM DTT yielded the best results (FIGS. 4C and 4D). The reducing agents tris(2-carboxyethyl)phosphine (TCEP) and beta-mercaptoethanol (BME) were also tested and both were observed to be inferior to DTT (FIG. 4C).

For optimized studies in FIGS. 4A-4D, samples were incubated at 37° C. for 1 hour using 20 ug of MsrAB (357 pmol) and 5 pmol of each peptide. All samples were analyzed on the Orbitrap® Classic (FIG. 4A) and Orbitrap® Elite (FIG. 4B-D).

For FIG. 4A, conditions included 100 mM TRIS HCl, 3 or 10 kDa Amicon® filter, 400 ul reaction volume, 15 mM DTT, washed 3 times with 400 ul water to desalt, eluted with 3 times 50% methanol, and desalted by C18 Ziptip® (Sigma Aldrich).

For FIG. 4B, conditions included 100 mM TRIS HCl or 100 mM Ammonium bicarbonate, 10 kDa Amicon® filter, 400 ul reaction volume, washed 3 times with 400 ul water to desalt, eluted with 3 times 50% methanol.

For FIG. 4C, conditions included 100 mM TRIS HCl, 10 kDa Amicon® filter, 400 ul reaction volume, 1-15 mM DTT, 15 mM TCEP or 1 ul beta-mercaptoethanol (BME), eluted with 3 times 50% methanol, and desalted in 10K filter.

For FIG. 4D, conditions included 100 mM ammonium bicarbonate, 10 kDa Amicon® filter, 400 ul reaction volume, 15, 30, 50 mM mM DTT, eluted with 3 times 50% methanol, and desalted in 10K filter.

Unspecific binding to the Amicon® membrane filters may be reduced if the filters are incubated with bovine serum albumin (BSA) prior to incubation with a methionine-containing peptide or protein.

Additionally, MsrAB protein was freeze dried on the membrane filter and was subsequently reactivated with buffer and DTT.

Figure 4E:
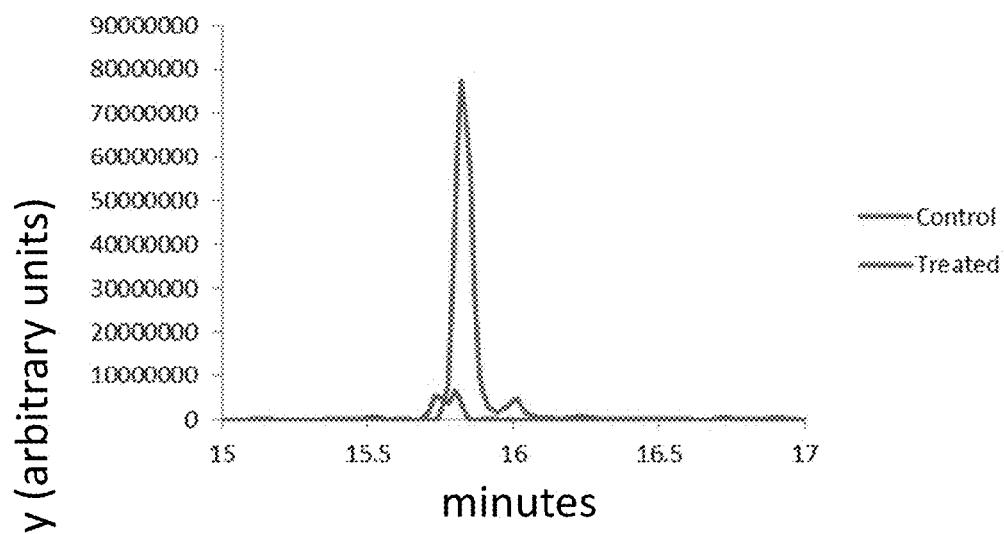
FIG. 4E shows MS XIC from GAILTTMLATR (SEQ ID NO: 2) peptide that was treated with Control Buffer (upper spectrum) or MsrAB (lower spectrum) with GAILTTM(ox)LATR oxidized peptide shown in blue and GAILTTMLATR reduced peptide shown in red, according to embodiments of the present invention.
Figure 4E:
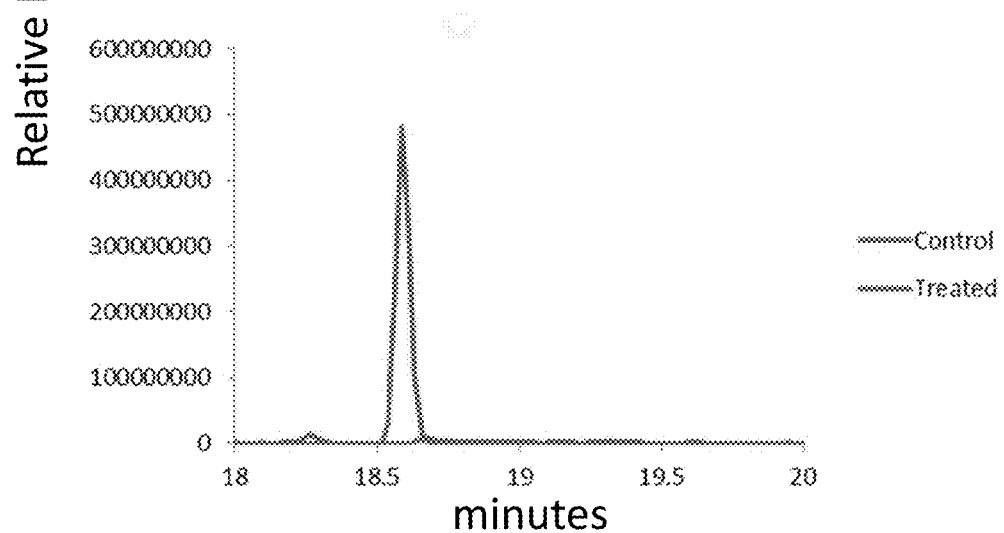

Using the optimized conditions obtained from studies shown in FIGS. 4A-4D, an almost completely oxidized GAILTTM(ox)LATR (SEQ ID NO: 2) was reduced using MsrAB. FIG. 4E shows two chromatograms where a complete reduction occurred (bottom, blue) vs. control (top, red). For the complete reduction of almost oxidized GAILTTM (ox)LATR (SEQ ID NO: 2) using MsrAB with the optimized conditions, samples were incubated at 37° C. for 1 hr using 20 ug of MsrAB=357 pmol and 5 pmol of peptide in 100 mM TRIS HCl pH 8, 10 kDa Amicon® filter, 400 ul reaction volume, 15 mM DTT, eluted with 3 times 50% methanol, desalted with C18 Ziptip®, and analyzed on Orbitrap® Elite.

Example 4. Global Proteomics Studies

Figure 5A:
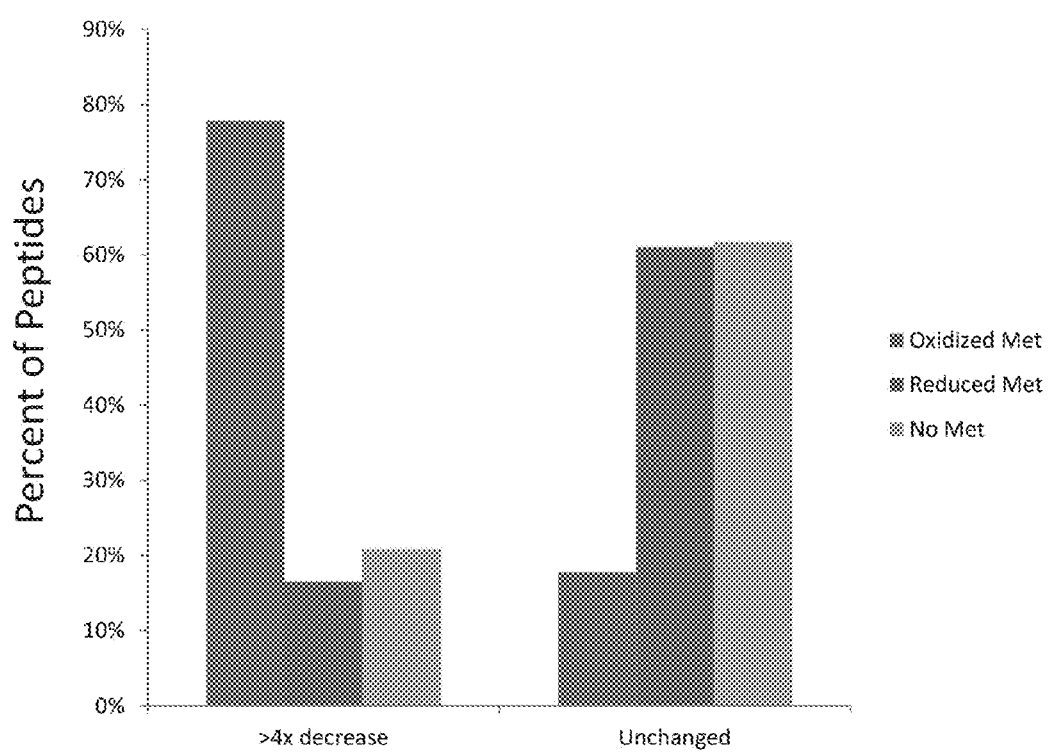
FIG. 5A is a histogram showing the percent of peptides (blue representing peptides having oxidized methionine, red representing peptides having reduced methionine, and green representing peptides have no methionines) from a MsrAB-treated trypsin digested HeLa lysate compared to the same peptides from an untreated (no MsrAB) trypsin digested HeLa lysate, in which the left set of peptides represent the relative amount of peptides in the lysate that showed greater than 4-fold decrease upon MsrAB treatment and the right set of peptides represent the relative amount of peptides in the lysate that showed no change upon MsrAB treatment, according to embodiments of the present invention.

The efficacy of methionine reduction in a global HeLa trypsin digest was analyzed. For this study, a sample was split with half of the sample treated with MsrAB enzyme and the other half with buffer alone. The intensities of the treated vs. untreated tryptic peptides were analyzed and the percentage of the ratios in the histogram are shown in FIG. 5A. Three categories of peptides were distinguished including peptides containing oxidized methionines (blue), peptides containing reduced methionines (red) and peptides not containing any methionines (green).

Under the optimized conditions as described above, the vast majority of oxidized peptides (>75%) showed at least a four-fold decrease after a single treatment with MsrAB, while approximately 15% remained unchanged (i.e. had a change of less than 4-fold). As expected, peptides containing reduced methionines (red) and peptides not containing any methionines (green) remained largely unchanged, although some losses due to sample handling were observed for these peptides.

For FIG. 5A, conditions included: samples were incubated at 37° C. for 1 hr, 20 ug of MsrAB=357 pmol were used with 1 pg of trypsinized HeLa lysate; 100 mM Ammonium bicarbonate pH 8, 10 kDa Amicon® filter, 400 ul reaction volume, 15 mM DTT, peptide was eluted with 3 times 50% methanol, desalted in 10 K filter, and analyzed on Orbitrap® Elite.

Figure 5B:
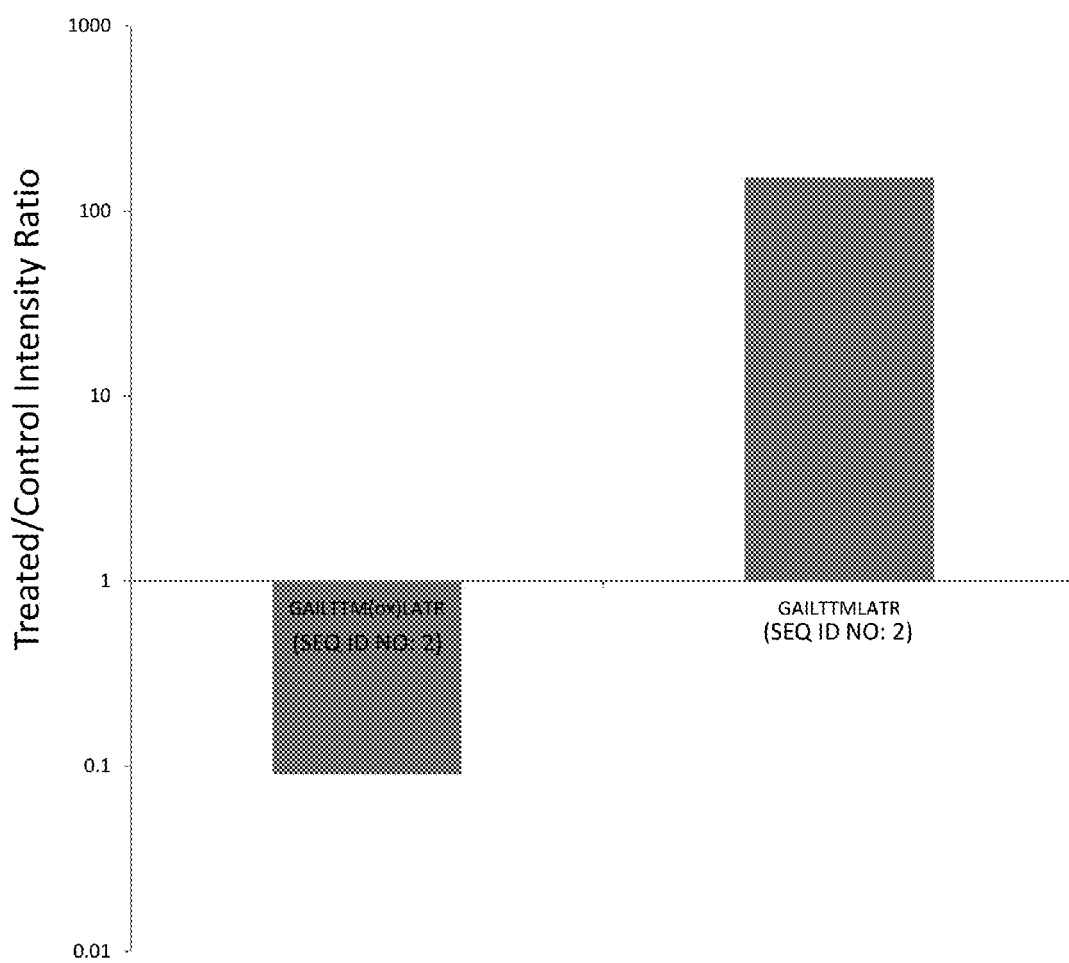
FIG. 5B is a graph showing the ratio of treated to control (treated/control) of GAILTTM(ox)LATR and GAILTTMLATR peptide when the GAILTTMLATR peptide is added to the trypsin digested HeLa lysate as shown in FIG. 5A and treated with MsrAB enzyme, showing that reduction by MsrAB of a particular peptide is effective in a complex HeLa digest background, according to embodiments of the present invention.

As shown in FIG. 5B, it was then tested whether similar results were achieved when the standard peptide GAILTTM(ox)LATR (SEQ ID NO: 2) was in a complex background such as a HeLa digest, where the standard peptide would need to compete for the reductive potential of MsrAB. This sample was analyzed in a targeted analysis using the QTRAP® (ThermoFisher Scientific). As shown in FIG. 5B, an approximate 10-fold decrease in the oxidized version of the standard peptide (SEQ ID NO: 2) and an approximate 100-fold increase in the reduced version of the peptide (SEQ ID NO: 2), showing that MsrAB was effective in reducing this standard peptide in a complex HeLa digest background. This method is therefore compatible with both targeted and untargeted proteomics analyses.

For FIG. 5B, conditions included: sample was incubated at 37° C. for 1 hr, 20 ug of MsrAB was used for 5 pmol of standard peptide (SEQ ID NO: 2) and 1 ug of HeLa tryptic digest, 100 mM TRIS HCl pH 8, 10 kDa Amicon® filter, 400 ul reaction volume, 15 mM DTT, eluted with 3 times 50% methanol, desalted with C18 Ziptip®, and analyzed on QTRAP®.

Example 5. Reduction of Methionine-Containing Proteins

Figure 6A:
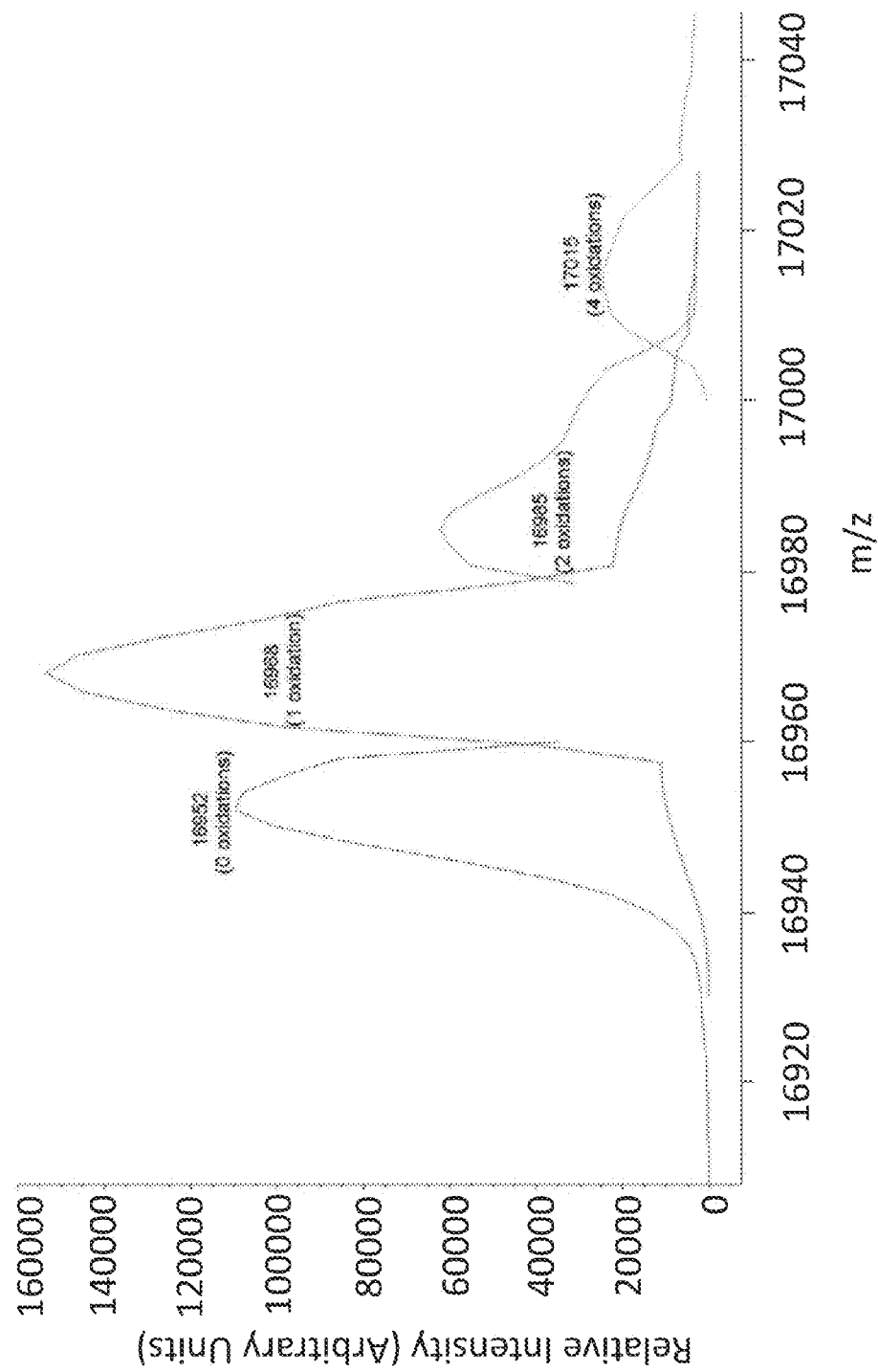
FIG. 6A shows a MS spectrum of the relative amounts of oxidized apomyoglobin protein (oxidized with 0.3% H2O2) used as the starting material prior to treatment with MsrAB enzyme, according to embodiments of the present invention.
Figure 6B:
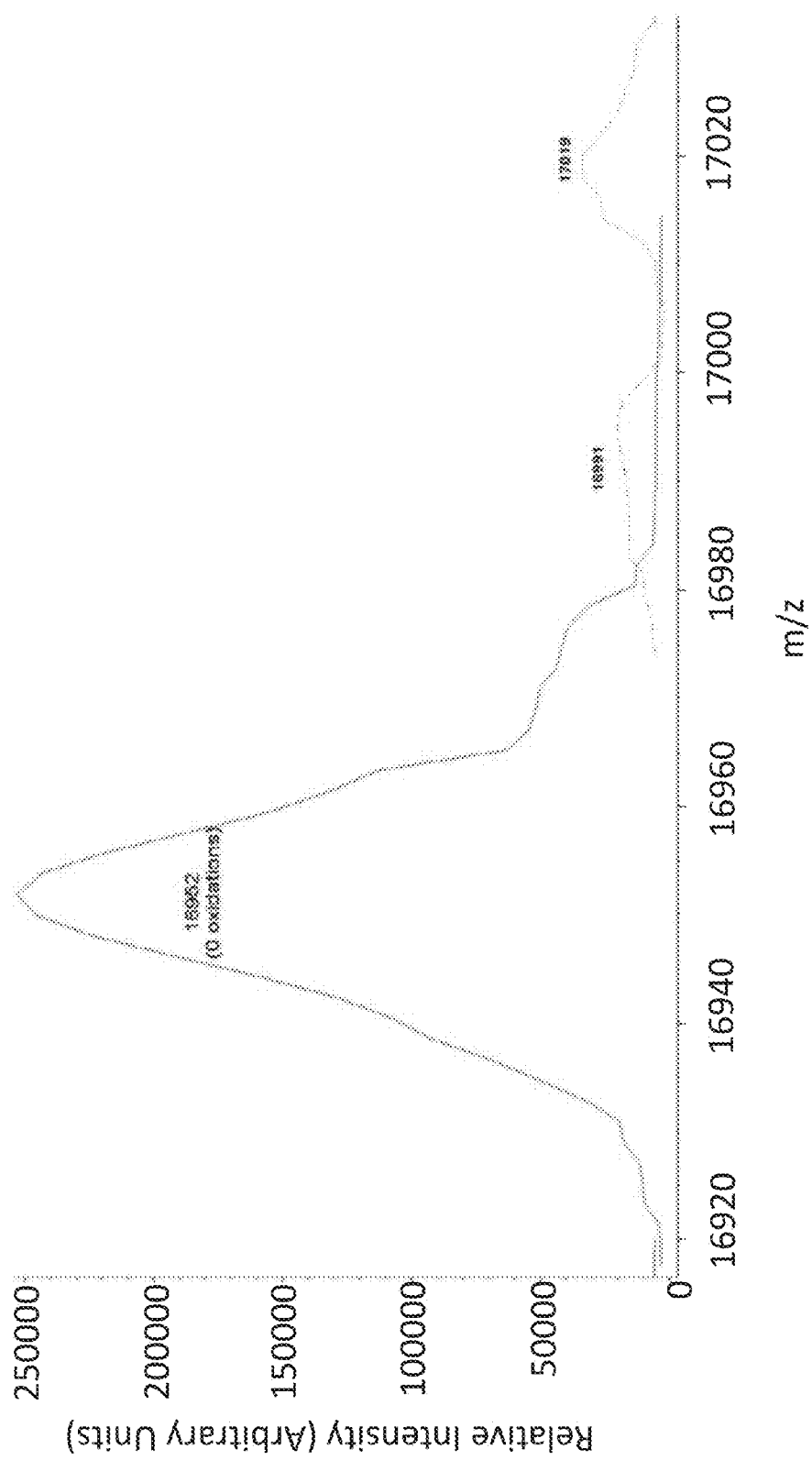
FIG. 6B shows a MS spectrum of the relative amounts of reduced apomyoglobin protein after 60 pmols of oxidized apomyoglobin was reacted with 20 ug of MsrAB enzyme in 80 mM TRIS HCl at pH 8.0 incubated for 1 hour at 37° C., and injected into a mass spectrometer, according to embodiments of the present invention.

To test whether MsrAB could also be used in conjunction with proteins, oxidized apomyoglobin was analyzed with MsrAB. As shown in FIGS. 6A, 6B, Met-oxidized apomyoglobin is completely reduced with MsrAB. Apomyoglobin contains two methionines and as shown in FIG. 6A, one methionine is predominantly oxidized over both methionines. Both of these oxidized methionines are completely eliminated in the reduced form as shown in FIG. 6B. It is noted that FIG. 6A also shows some minor components indicating oxidation of other residues (i.e.; tryptophan).

For FIGS. 6A-6B, conditions included 60 pmol of oxidized apomyoglobin reacted with 20 ug of MsrAB, 80 mM TRIS HCl pH8.0 incubated for 1 hr at 37° C., and injected in MSD.

Example 6. Sample Preparation

Standard peptides TAGTSFMMTPYVVTR (SEQ ID NO: 1) and GAILTTMLATR (SEQ ID NO: 2) were purchased from JPT (Berlin, Germany). iRT peptides were from Biognosys (Zurich, Switzerland). MrsA, apomyoglobin and HeLa digest were purchased from Thermo Fisher (San Jose, Calif.). Affi-Gel® 10 was purchased from Biorad® (Hercules, Calif.). Amicon® filters were purchased from EMD Millipore® (Billerica, Mass.).

Example 7. MrsA-Bead Preparation

Affi-Gel 10 was buffer exchanged from 50 mM Tris, pH 7.6 to 50 mM MOPS, pH7.4. MsrA (0.71 nmol=20 µg) was coupled to the 100 µl slurry of Affi-Gel10 and free remaining sites were blocked with 100 mM Tris. MsrA was reduced with 15 mM DTT in 25 mM TRIS, pH 7.4 for 15 min at 37° C. Standard peptides SEQ ID NOs. 1-2 (10 pmol) was reacted with MsrA-slurry for 1 hr at 37° C. Peptides were eluted with 25 mM TRIS, pH 7.4, desalted using ZIP-tips and dried down prior to LC-MS/MS analysis.

Example 8. Gene Synthesis and Recombinant MrsAB Expression

MsrAB DNA (SEQ ID NO: 3) from *Neisseria meningitidis* was subcloned to express MSRAB protein (SEQ ID NO: 4) including a C-terminal His-tag (SEQ ID NO: 5). SEQ ID NO: 3 was synthesized by GenScript, optimized for expression in *E. coli*, and cloned into PET-3A vectors with NdeI-BamHI Amp cloning restriction sites. MsrAB-expressing plasmids were transfected into *E. coli* cells and secreted MsrAB was isolated from the medium using protein Ni affinity columns.

```
SEQ ID NO: 3: Gene Name: MRSAB, Length: 1599 bp,
Vector Name: pUC57,
CATATGAAACATCGTACCTTCTTCTCCCTGTGTGCTAAATTTGGCTGCCT

GCTGGCCCTGGGTGCCTGTAGTCCGAAAATCGTTGACGCTGGTGCCGCAA

CCGTCCCGCATACCCTGTCCACCCTGAAAACCGCAGATAACCGTCCGGCT

TCAGTTTATCTGAAGAAAGATAAACCGACCCTGATTAAATTCTGGGCCTC

CTGGTGCCCGCTGTGTCTGTCAGAACTGGGCCAGACGGAAAAATGGGCGC

AAGATGCCAAATTTAGCTCTGCAAACCTGATCACCGTGGCTTCACCGGGC

TTTCTGCACGAAAAGAAAGATGGTGACTTCCAGAAATGGTATGCAGGCCT

GAATTACCCGAAACTGCCGGTGGTTACGGATAACGGCGGTACCATTGCAC

AATCACTGAATATCTCGGTTTATCCGAGCTGGGCTCTGATTGGCAAAGAT

GGTGACGTGCAGCGTATTGTTAAAGGTAGTATCAACGAAGCCCAAGCACT

GGCTCTGATCCGCGATCCGAATGCGGACCTGGGCTCTCTGAAACATAGTT

TCTACAAACCGGATACCCAGAAGAAAGATTCTAAAATCATGAACACCCGT

ACGATCTATCTGGCGGGCGGTTGCTTTTGGGGTCTGGAAGCCTACTTCCA

GCGCATTGATGGCGTCGTGGACGCCGTGAGTGGCTATGCCAACGGTAATA
```

```
-continued
CGAAAAATCCGTCCTATGAAGATGTTTCATACCGTCATACCGGTCACGCA

GAAACGGTTAAAGTCACCTATGATGCTGACAAACTGTCTCTGGATGACAT

CCTGCAGTACTTTTTCCGTGTTGTCGATCCGACGTCGCTGAACAAACAGG

GCAATGACACCGGTACGCAATATCGCAGCGGCGTCTATTACACCGATCCG

GCAGAAAAGCTGTGATTGCAGCTGCGCTGAAACGCGAACAGCAAAAATA

TCAGCTGCCGCTGGTTGTGGAAAACGAACCGCTGAAAAATTTCTACGATG

CGGAAGAATATCATCAAGACTACCTGATCAAAAACCCGAATGGTTATTGT

CACATTGATATCCGTAAAGCGGACGAACCGCTGCCGGGCAAAACCAAAAC

GGCCCCGCAGGGCAAAGGTTTTGATGCCGCAACCTATAAAAAACCGTCCG

ACGCCGAACTGAAACGCACCCTGACGGAAGAACAGTACCAAGTGACGCAG

AATTCGGCGACCGAATATGCCTTTAGCCATGAATACGATCACCTGTTCAA

ACCGGGTATTTATGTTGACGTCGTGAGCGGCGAACCGCTGTTTAGTTCCG

CAGATAAATACGACTCTGGCTGCGGTTGGCCGAGTTTCACGCGTCCGATC

GATGCGAAATCTGTGACCGAACATGATGACTTTAGTTATAACATGCGTCG

CACCGAAGTTCGCTCGCACGCTGCGGATAGCCATCTGGGCCACGTCTTTC

CGGATGGTCCGCGTGACAAAGGCGGTCTGCGCTACTGTATTAATGGTGCC

AGCCTGAAATTTATCCCGCTGGAACAAATGGACGCTGCCGGTTATGGCGC

TCTGAAATCAAAAGTCAAACATCATCACCATCACCACTAGTAAGGATCC.

SEQ ID NO: 4: Neisseria meningitidis serogroup A/
serotype 4A (strain Z2491)
MKHRTFFSLCAKFGCLLALGACSPKIVDAGAATVPHTLSTLKTADNRPAS

VYLKKDKPTLIKFWASWCPLCLSELGQTEKWAQDAKFSSANLITVASPGF

LHEKKDGDFQKVVYAGLNYPKLPVVTDNGGTIAQSLNISVYPSWALIGKD

GDVQRIVKGSINEAQALALIRDPNADLGSLKHSFYKPDTQKKDSKIMNTR

TIYLAGGCFWGLEAYFQRIDGVVDAVSGYANGNTKNPSYEDVSYRHTGHA

ETVKVTYDADKLSLDDILQYFFRVVDPTSLNKQGNDTGTQYRSGVYYTDP

AEKAVIAAALKREQQKYQLPLVVENEPLKNFYDAEEYHQDYLIKNPNGYC

HIDIRKADEPLPGKTKTAPQGKGFDAATYKKPSDAELKRTLTEEQYQVTQ

NSATEYAFSHEYDHLFKPGIYVDVVSGEPLFSSADKYDSGCGWPSFTRPI

DAKSVTEHDDFSYNMRRTEVRSHAADSHLGHVFPDGPRDKGGLRYCINGA

SLKFIPLEQMDAAGYGALKSKVK.

SEQ ID NO: 5: Target Vector: pET-3a, Cloning Site:
NdeI-XhoI, Comment: Please use the in-house
commercial pET-3a provided by GenScript.
MKHRTFFSLCAKFGCLLALGACSPKIVDAGAATVPHTLSTLKTADNRPAS

VYLKKDKPTLIKFWASWCPLCLSELGQTEKWAQDAKFSSANLITVASPGF

LHEKKDGDFQKVVYAGLNYPKLPVVTDNGGTIAQSLNISVYPSWALIGKD

GDVQRIVKGSINEAQALALIRDPNADLGSLKHSFYKPDTQKKDSKIMNTR

TIYLAGGCFWGLEAYFQRIDGVVDAVSGYANGNTKNPSYEDVSYRHTGHA

ETVKVTYDADKLSLDDILQYFFRVVDPTSLNKQGNDTGTQYRSGVYYTDP

AEKAVIAAALKREQQKYQLPLVVENEPLKNFYDAEEYHQDYLIKNPNGYC

HIDIRKADEPLPGKTKTAPQGKGFDAATYKKPSDAELKRTLTEEQYQVTQ

NSATEYAFSHEYDHLFKPGIYVDVVSGEPLFSSADKYDSGCGWPSFTRPI

DAKSVTEHDDFSYNMRRTEVRSHAADSHLGHVFPDGPRDKGGLRYCINGA

SLKFIPLEQMDAAGYGALKSKVKHHHHHH.
```

Example 9. MsrAB Assay

Amicon® (Amicon® Ultra 0.5 mL centrifugal filter) filters with a 10 k cutoff were washed with 3×500 μL mL of 50% methanol, followed by preconditioning with 3×500 μL of 100 mM TRIS, pH 8 or 100 mM ammonium bicarbonate, pH 8.0, respectively. An aliquot (20 μL of 2.43 μg/μL) of MsrAB was added to the preconditioned Amicon® filter and the enzyme was activated with 500 μL reductant and incubated with oxidized methionine-containing peptides (5 pmol or 1 μg of trypsinized HeLa lysate) at 37° C. for 30 min. Reduced peptides were washed three times with water, eluted with 3×50% methanol. Samples were evaporated in vacuo and re-dissolved in 0.2% formic acid and analyzed by LC-MS/MS.

Example 10. Optimization Studies

GAILTTMLATR (SEQ ID NO: 2) standard peptide (5 pmol) was used for optimizing the enzymatic reaction conditions. 3 kDa vs. 10 kDa Amicon® filters, ammonium bicarbonate vs. TRIS buffer, various DTT concentrations and TCEP and beta-mercaptoethanol were tested. Select samples were spiked with internal retention time (iRT) standard peptides (500 fmol).

Example 10. Optimization Studies

GAILTTMLATR (SEQ ID NO: 2) standard peptide (5 pmol) was used for optimizing the enzymatic reaction conditions. 3 kDa vs. 10 kDa Amicon filters, ammonium bicarbonate vs. TRIS buffer, various DTT concentrations and TCEP and beta-mercaptoethanol were tested. Select samples were spiked with internal retention time (iRT) standard peptides (500 fmol).

To test the capacity of MsrAB to reduce oxidized peptides in a complex background, 5 pmol standard peptide (SEQ ID NO: 2) and 500 fmol iRT was spiked into 1 ug of a trypsin digested HeLa lysate and evaluated by targeted QTRAP® analysis.

Example 11. Lyophilization of MsrAB on Amicon® Filters

Amicon® filters were washed as described above and 20 μL of 2.43 μg/μL of MsrAB was added to the filter before freeze-drying. The lyophilized filters were reactivated with 500 μL reducing agent (DTT or thioredoxin) and used as described above.

Example 12. Intact Proteins

Oxidized apomyoglobin (60 pmol) was reacted with 20 μg of DTT-activated MsrAB in 80 mM TRIS HCl pH 8.0, incubated for 1 hr at 37 C, and analyzed by LC-MS using an Agilent (Santa Clara, Calif.) MSD without separation of MsrAB and protein apomyoglobin.

Example 13. Nanoflow Liquid Chromatography Tandem Mass Spectrometry (NanoLC-MS/MS)

Initial experiments were performed on a nanoflow liquid chromatography system, EASY-nLC® II coupled to an Orbitrap® Classic mass spectrometer, equipped with a nanoelectrospray ion source (all Thermo Fisher Scientific, Bremen, Germany). For the EASY-nLC™ II system, solvent A was 0.2% formic acid in 98.8% water and 1% acetonitrile, and solvent B was 0.2% formic acid in 80% acetonitrile and 19.8% water. The peptides were separated on a 16 cm analytical column (75 µm ID) packed in-house with Reprosil-Pur® C18AQ resin (3 µm, 120 Å pore size, Dr. Maisch, Ammerbuch, Germany) at a flow rate of 350 nL/min. The column was heated to 40° C. The peptides were eluted using a 35 min-gradient: 0-4% Solvent B (5 min), 4-72% B (30 min), 72-100% B (30 min), and 100% B (4 min). The Orbitrap® was operated to automatically switch between a full scan (m/z=400-1600) in the Orbitrap® and 10 CID MS/MS scans in the linear ion trap. CID was performed with helium as collision gas at a normalized collision energy of 35% and 10 ms of activation time, essentially as described in Kalli and Hess, Proteomics, 2012, 12:21-31 and Kalli et al., J. Proteome Res., 2013, 12:3071-3086, the entire contents of both of which are incorporate herein by reference.

Global HeLa digested samples were analyzed on a nanoflow liquid chromatography system, EASY-nLC® 1000 coupled to an Orbitrap® Elite mass spectrometer, equipped with a nanoelectrospray ion source (all Thermo Fisher Scientific, Bremen, Germany). The solvent and column were the same as described above. The peptides were eluted using a 170 min-gradient: 0-2% Solvent B (5 min), 2-30% B (155 min), 30-100% B (1 min), and 100% B (9 min). The Orbitrap® Elite was operated to automatically switch between a full scan (m/z=400-1600) in the Orbitrap® and 20 CID MS/MS scans in the linear ion trap. CID was performed with helium as collision gas at a normalized collision energy of 35% and 10 ms of activation time, essentially as described in Kalli and Hess, 2012, supra, and Kalli et al., 2013, supra.

Example 14. Nanoflow Liquid Chromatography Multiple Reaction Monitoring (NanoLC-MRM)

Targeted experiments were performed on an Eksigent ekspert nanoLC 425 pump, ekspert nanoLC400 autosampler, ekspert cHiPLC® (Eksigent, Dublin, Calif.), coupled to a NanoSpray® III Source and Heated Interface on a QTRAP® 6500 (AB Sciex, Framingham, Mass.). The system was controlled with Analyst software. Peptides were concentrated using a 0.5 mm long, 200 µm ID cHiPLC Chrom XP C18-CL trap column (3 µm particle size, 120A) and separated by a 150 mm long, 75 µm ID cHiPLC® Chrom XP C18-CL column (3 µm particle size, 120A) at a column temperature of 40° C. and a flow rate of 300 nL/min. Solvent A was 0.2% formic acid and solvent B was 98.8% acetonitrile containing 0.2% formic acid. Linear gradients from 0 to 30% B are used within 30 min, 30-100% B in 1 min, followed by 100% B for 10 min. Mass spectra were initially recorded in positive ion mode acquiring data from the transition lists obtained from the Orbitrap® to confirm correct peak identification. Optimization of declustering potentials and collision energy was done automatically in Skyline. Quantitative analyses were performed using MRM scheduling in QQQ mode.

Example 15. LC-MSD Intact Protein Analysis

Intact protein samples were analyzed on an HP1100 MSD SL mass spectrometer. Solvent A was 5% acetic acid, solvent B was acetonitrile. A Zorbax® 300SB-C3 column (2.1×150 mm, 5 micron) was used with the following gradient: 0-5% Solvent B (5 min), 5-95% B (20 min), 95% B (10 min), and 100% B (8 min) at a flow rate of 200 µL/min and a column temperature of 40° C. Electrospray voltage was set to 4000 V and after a 5 min delay, the samples were directed into the mass spectrometer, which scanned all ions in the 500-1700 m/z range.

Example 16. Data Analysis

For individual peptide analysis, raw files were loaded into Skyline and areas under the extracted ion chromatograms were used to quantify the relative peptide abundance. For lysate analysis, raw files were loaded into MaxQuant and searched against the UniProt human database (91647 sequences) and a contaminant database (245 sequences). Methionine oxidation and protein N-terminal acetylation were specified as variable modifications and carboxyamidomethylation of cysteine was a fixed modification. Trypsin was specified as the digestion enzyme and up to two missed cleavages were allowed. False discovery rates were fixed to be less than 1% and were estimated by searching a reversed version of the sequence database. Precursor mass tolerance was less than 4.5 ppm after recalibration and fragment mass tolerance was 0.5 Da.

While the present invention has been illustrated and described with reference to certain exemplary embodiments, those of ordinary skill in the art will understand that various modifications and changes may be made to the described embodiments without departing from the spirit and scope of the present invention, as defined in the following claims.

What is claimed is:

1. A method for reducing a methionine containing peptide or protein for mass spectrometry analysis, comprising:
obtaining a heterologous methionine sulfoxide reductase (Msr) enzyme composition comprising a heterologous Msr protein expressed and isolated from a host cell, the heterologous Msr enzyme composition comprising:
a heterologous MsrA protein and a heterologous MsrB protein,
a heterologous MsrAB protein from *Neisseria*, or
a combination thereof;
immobilizing the heterologous Msr enzyme composition on a surface to form an immobilized heterologous Msr enzyme composition,
incubating the methionine containing peptide or protein with the immobilized heterologous Msr enzyme composition; and
separating the methionine containing peptide or protein from the immobilized heterologous Msr enzyme composition after the incubating.

2. The method of claim 1, wherein immobilizing the heterologous Msr enzyme composition comprises coupling the heterologous Msr enzyme composition to resin beads or adding the heterologous Msr enzyme composition to a membrane filter.

3. The method of claim 1, wherein immobilizing the heterologous Msr enzyme comprises adding the heterologous Msr enzyme composition to a membrane filter, and incubating the the methionine containing peptide or protein comprises adding bovine serum albumin (BSA) to the membrane filter.

4. The method of claim 1, further comprising activating the heterologous Msr enzyme composition prior to incubating the methionine containing peptide or protein.

5. The method of claim 4, wherein activating the heterologous Msr enzyme composition comprises incubating the heterologous Msr enzyme composition with a reducing agent.

6. The method of claim 5, wherein the reducing agent is dithiothreitol (DTT) or thioredoxin.

7. The method of claim 1, wherein incubating the methionine containing peptide or protein to the immobilized heterologous Msr enzyme composition further comprises adding a Tris or ammonium bicarbonate buffer.

8. A method for preparing a methionine containing peptide or protein for mass spectrometry analysis, comprising:
obtaining a heterologous methionine sulfoxide reductase (Msr) enzyme composition comprising a heterologous Msr protein expressed and isolated from a bacterial, yeast, or human host cell, the heterologous Msr enzyme composition comprising:
- a heterologous MsrA protein and a heterologous MsrB protein,
- a heterologous MsrAB protein from *Neisseria*, or
- a combination thereof;

immobilizing the heterologous Msr enzyme composition on a resin bead or a membrane filter to form an immobilized heterologous Msr enzyme composition;

activating the immobilized heterologous Msr enzyme composition to form an activated heterologous Msr enzyme composition;

adding the methionine containing peptide or protein to the activated heterologous Msr enzyme composition; and separating the methionine containing peptide or protein from the activated heterologous Msr enzyme composition.

9. The method of claim 8, wherein activating the immobilized heterologous Msr enzyme composition comprises washing or incubating with dithiothreitol or thioredoxin.

10. A kit for reducing a methionine containing peptide or protein according to the method of claim 1, the kit comprising the heterologous Msr protein expressed and isolated from the host cell.

11. The kit of claim 10, wherein the heterologous Msr protein is a heterologous MsrA protein, a heterologous MsrB protein, and/or a heterologous MsrAB protein.

12. The kit of claim 10, wherein the heterologous Msr protein is a heterologous MsrAB protein.

13. The kit of claim 10, wherein the heterologous Msr protein is lyophilized on a membrane filter.

14. The kit of claim 10, further comprising a blocking agent.

15. The kit of claim 10, wherein the heterologous Msr protein is coupled to a resin bead.

16. The kit of claim 10, further comprising Tris or ammonium buffer.

17. The kit of claim 10, further comprising dithiothreitol (DTT) or thioredoxin.

18. A kit for preparing a methionine containing peptide or protein according to the method of claim 8, the kit comprising the heterologous Msr protein expressed and isolated from the host cell.

19. The kit of claim 18, wherein the heterologous Msr protein is a heterologous MsrAB protein.

20. The kit of claim 18, wherein the heterologous Msr protein is lyophilized on a membrane filter.

* * * * *

UNITED STATES PATENT AND TRADEMARK OFFICE
CERTIFICATE OF CORRECTION

| | | |
|---|---|---|
| PATENT NO. | : 10,266,866 B2 | Page 1 of 1 |
| APPLICATION NO. | : 15/360662 | |
| DATED | : April 23, 2019 | |
| INVENTOR(S) | : Michael Sweredoski et al. | |

It is certified that error appears in the above-identified patent and that said Letters Patent is hereby corrected as shown below:

On the Title Page

In Column 2, item (56), other publications, Line 7     delete ""Methionine sulfoxide reductase a" and insert -- "Methionine sulfoxide reductase A --

In the Claims

In Column 22, Line 47, Claim 3     delete "the the" and insert -- the --

Signed and Sealed this
Third Day of November, 2020

Andrei Iancu
*Director of the United States Patent and Trademark Office*